United States Patent [19]

Tolgyesi et al.

[11] 4,344,763

[45] Aug. 17, 1982

[54] REACTIVE SILICONE HAIR SETTING COMPOSITIONS

[75] Inventors: Eva Tolgyesi; Ann F. Bresak, both of Rockville, Md.

[73] Assignee: The Gillette Company, Boston, Mass.

[21] Appl. No.: 851,748

[22] Filed: Nov. 15, 1977

[51] Int. Cl.$^3$ ............................................... A61K 7/11
[52] U.S. Cl. ..................................... 8/127.51; 8/127.6;
    132/7; 424/DIG. 1; 424/DIG. 2; 424/47;
    424/70; 424/71; 424/184; 524/857
[58] Field of Search .................. 260/33.4 SB, 33.6 SI;
    424/71, 70, 47, DIG. 1, DIG. 2, 184; 8/127.51,
    127.6, 181; 132/7

[56] References Cited

U.S. PATENT DOCUMENTS

| | | | |
|---|---|---|---|
| 2,782,790 | 2/1957 | Hersh et al. | 132/7 |
| 2,970,126 | 1/1961 | Brown | 260/33.6 SI |
| 3,248,296 | 4/1966 | Steinbach et al. | 424/71 |
| 3,334,119 | 8/1967 | Cohen | 424/184 X |
| 3,392,040 | 7/1968 | Kass | 424/70 X |
| 3,418,266 | 12/1968 | Nielsen | 260/33.4 SI |
| 3,846,359 | 11/1974 | Rostaing | 260/33.4 SI |
| 3,876,459 | 4/1975 | Burrill et al. | 8/127.6 X |
| 3,928,558 | 12/1975 | Cheesman et al. | 424/47 |

FOREIGN PATENT DOCUMENTS 1434017 4/1976 United Kingdom ................ 8/127.6

OTHER PUBLICATIONS

Sardo, American Cosmetics and Perfumery, vol. 87, pp. 43, 44 and 46, (Dec. 1972).

*Primary Examiner*—Natalie Trousof
*Assistant Examiner*—Vera C. Clarke
*Attorney, Agent, or Firm*—Leonard J. Janowski

[57] ABSTRACT

Reactive silicone hair setting compositions composed of isopropanol solutions containing at least one aminoalkylalkoxysilane and a titanate ester. Optional ingredients include hair conditioners and tetraalkoxysilanes. The compositions provide high set holding levels at high humidities.

10 Claims, No Drawings

REACTIVE SILICONE HAIR SETTING COMPOSITIONS

BACKGROUND OF THE INVENTION

1. Field of the Invention

This invention relates to hair setting compositions, and more particularly, to reactive silicone hair setting compositions.

2. Description of the Prior Art

The use of reactive silicone compositions for setting hair is well known in the prior art. For instance, U.S. Pat. No. 2,782,790, issued to Hersh et al, describes organo-silanes having at least two but less than four hydrolyzable groups selected from the class consisting of alkoxy, aryloxy and acyloxy radicals and alkoxy, aryloxy and acyloxy radicals together with a halogen group selected from the class consisting of chlorine and bromine. In the process described in the patent, the hair to be treated is wet with water either before or after the application of the organo-silane and then set into the desired shape. The water reacts with the hydrolyzable groups, forming the corresponding silanol, which polymerizes to hold the hair in place.

An improvement on the basic technology is described in an article entitled "New Types of Hair Setting Sprays having Semi-Permanent Properties", by Fulvio Sardo in Vol. 87, *American Cosmetics and Perfumery*, Pages 43-46 (December 1972). That article describes the use of alkyl titanates as catalysts for the polymerization of siloxanes. The compounds are used in a manner similar to that described in Hersh above, in that the hair is wet after which the composition is applied to the hair as a nonaqueous lotion or spray.

British Pat. No. 1,434,017, issued to Burrill et al, describes a process for shrinkproofing wool employing compositions containing (A) a polydiorganosiloxane having terminal silicon bonded hydroxyl radicals and a molecular weight of at least 750; (B) an organosilane of the general formula $RSiR'_nX_{3-n}$ in which the R radical contains at least two amino groups; (C) a catalyst, e.g., a titanate ester and/or a silane of the formula $R''_mSiZ_{4-n}$ wherein Z is an alkoxy radical having 1-4 carbon atoms, and m is 0 or 1; and (D) a solvent which is a hydrocarbon or chlorinated hydrocarbon such as toluene, xylene, white spirit, or perchloroethylene. While ingredients (B) and (C) are also used in the present invention; the difference in solvents employed and the addition of ingredient (A) result in the cured composition of Burrill being an oil, which lacks the physical strength needed to retain hair in a desired configuration.

A disadvantage of conventional non-silicone prior art hair setting agents is that they are ineffective at high humidities. While reactive silicone hair setting agents have solved the problem to a certain extent, they have suffered from the disadvantage that the time required for curing has been excessive. Thus, a need exists for compositions which may be polymerized more rapidly, but still give good set holding even after prolonged exposure to high humidities.

SUMMARY OF THE INVENTION

The present invention comprises a composition for imparting a set to hair comprising an isopropanol solution containing:

(1) from about 0.5% to about 15% by weight of at least one aminoalkylalkoxysilane having the formula $$R_1NH(CH_2)_nSi(OR_2)_3$$

wherein
$R_1$ is $-H$, $-CH_3$, $-CH_2NH_2$, $-(CH_2)_2NH_2$, $$-\underset{\underset{O}{\|}}{C}NH_2, \text{ or } -(CH_2)_2NH(CH_2)_2\underset{\underset{O}{\|}}{C}OCH_3,$$

$R_2$ is methyl, ethyl, propyl, isopropyl, butyl, or isobutyl, and n is selected from the values 2 and 3; and (2) from about 0.0005% to about 1.5% by weight of a titanate ester having the formula $$(R_3O)_4Ti$$

wherein $R_3$ is methyl, ethyl, propyl, isopropyl, butyl, or isobutyl.

The weight ratio of titanate ester to aminoalkylalkoxysilane is from about 1:1000 to about 1:10.

DESCRIPTION OF THE PREFERRED EMBODIMENTS

The present invention is included within the class of hair setting agents which leave a thin layer of film-forming material on the hair. When the coated hair is dried in a desired configuration imposed by curlers, pins, etc., the thin layer of film-forming material tends to maintain the hair in the shape in which it was dried, resisting the tendency to revert to the initial configuration. Since this class of products accomplishes only a reversible physicomechanical change, the result is only temporary. In contrast, chemical hair treatments actually react with the keratin in the hair, thereby permanently modifying the structure of the hair keratin.

The present invention comprises three basic ingredients: (1) at least one aminoalkylalkoxysilane; (2) a titanate ester; and (3) a solvent which is preferably mainly isopropanol, although up to 15% of the total composition may be methanol, ethanol, or other chemically compatible solvent (i.e., not reactive with alkoxy silane) without interfering to any great extent with the polymerization process described below. Certain of the aminoalkylalkoxysilanes useful in the present invention are available commercially only in methanol solution. Thus, while it is preferred that isopropanol be the single solvent, methanol introduced into the system with the aminoalkylalkoxysilane is acceptable in the practice of the present invention. Isopropanol is also preferred to minimize the effect of any interaction between the titanate ester and other alcoholic solvents. Once the ingredients of the present invention have been combined, the titanate ester and solvent alcohol may undergo ester interchange, thereby affecting the reactivity of the catalyst. Any interchange occurring when isopropanol is the solvent produces an isopropyl titanate, the preferred titanate ester.

The polymerization process begins when the composition comes into contact with water on the hair. Water hydrolyzes the alkoxy portions of the aminoalkylalkoxysilanes of the present invention to hydroxyl groups. The titanate ester then catalytically reacts with the hydrolyzed aminoalkylalkoxysilane to form long chain polymers of the hydrolyzed aminoalkylalkoxysilane. While the reaction occurs readily at room temperature, it is preferred to speed up the reaction by the addition of heat. This may be accomplished, for example, by a salon-style hair dryer. The heat speeds up the evaporation of the solvent and the alcohol which is produced as a by-product of the reaction. A complete cure cannot be expected until all the solvents have been removed from the system. A more complete description of the polymerization process is set out in the Sardo article, supra.

Examples of preferred silanes according to the invention are:

gamma-aminopropyltriethoxysilane (A-1100 Silane, Union Carbide Corp., New York, N.Y.)

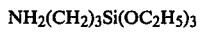

gamma-ureidopropyltriethoxysilane (A-1160 Silane, Union Carbide Corp., New York, N.Y.)

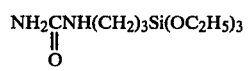

methyl[2-(3-trimethoxysilylpropylamino)-ethylamino]-3-propionate (C-600 Silane, Dow Corning Corp., Midland, Mich.)

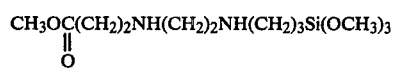

N-(2-aminoethyl)-3-aminopropyltrimethoxysilane (Z-6020, Dow Corning Corp., Midland, Mich.)

N-methyl-3-aminopropyltrimethoxysilane (PCR, Inc., Gainesville, Fla.)

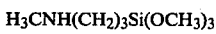

While individual silanes can be used in formulating the compositions of this invention, it is preferred to use mixtures of two or more silanes. A preferred combination is methyl [2-(3-trimethoxysilylpropylamino)-ethylamino]-3-propionate with gamma-ureidopropyl-triethoxysilane. Best results are obtained when the two aminoalkylalkoxysilanes are present in an equimolar ratio. The total percent by weight of individual or mixed aminoalkylalkoxysilane in the composition should be from 0.5 to 15, more preferably between 1 and 7.5.

Titanate esters useful in the practice of the present invention are those having the formula $(R_3O)_4Ti$ wherein $R_3$ is methyl, ethyl, propyl, isopropyl, butyl, or isobutyl. The most preferred titanate ester is tetraisopropyl titanate. The ratio of titanate ester to silane should be from about 1:1000 to about 1:10, more preferably from about 1:200 to about 1:20.

The set holding capabilities of the compositions of this invention can be further enhanced by the addition of a tetraalkoxysilane having the formula $Si(OR_4)_4$ wherein $R_4$ is methyl, ethyl, propyl, isopropyl, butyl, or isobutyl. Particularly preferred is tetraethoxysilane. While even small amounts of tetraalkoxysilane result in enhanced holding, it is preferred that the molar ratio of tetraalkoxysilane to aminoalkylalkoxysilane be from about 1:4 to about 9:4. More preferably, the ratio should be 3:4, which results in a solution where the number of alkoxy groups from the tetraalkoxysilane is equal to the number of alkoxy groups from the aminoalkylalkoxysilane. The total amount of all silanes in the composition should be kept in the range described above for aminoalkylalkoxysilanes. Thus, the tetraalkoxysilane should be used in place of a portion of the aminoalkylalkoxysilane at higher total silane concentration and the amount of titanate ester should be calculated on the basis of total reactive silanes.

Another optional ingredient is a conditioner for enhancing the combability of the hair after the composition has been applied. Any of the non-reactive conditioners described in the prior art will work including quaternary ammonium compounds (e.g., stearyldimethylbenzylammonium chloride), pyridinium derivatives (e.g., lauric acid ester of colaminoformylmethyl-pyridinium chloride), nonreactive polysiloxanes (e.g., DOW 200 fluid, a polydimethylsiloxane, 10 cs viscosity, Dow Corning Corp., Midland, Mich.), and paraffin oils (e.g., Fisher Light Domestic paraffin Oil, 125/135 Saybolt viscosity, Fisher Scientific Co., Pittsburgh, Pa.). While even very small amounts of conditioner will assist in combing, it is preferred that the percent by weight of the conditioner in the total composition be from about 0.005% to about 2.0%. Types of conditioner which should not be used in the present system include those having hydroxyl or free carboxyl groups such as fatty acids and ethylene oxide condensation products. Such compounds may interfere with the polymerization process giving films that are tacky, oily, or otherwise undesirable.

The compositions of the present invention are prepared by adding the silanes to the alcohol and mixing, followed by the addition of the titanate with stirring. Once the mixing has been completed, the composition is kept in a closed container to prevent premature polymerization induced by moisture from the atmosphere.

To use the compositions of the present invention to treat hair, the hair is preferably first wet with water, although the wetting can be postponed until after the composition is applied, if desired. While the hair need not be cleaned prior to wetting, the adhesion of the cured composition is enhanced if oil and dirt have previously been removed from the hair by shampooing. The composition is then applied using an applicator (e.g., a cotton swab) or by spraying (e.g., a pump spray). A typical amount of composition to be applied when the composition contains 3.5% by weight of active ingredients would be approximately 0.2 cc per gram of hair. The composition is then combed through the hair, and the hair set on rollers and allowed to dry. If desired, a hair dryer can be used to speed the curing process, since a complete cure is not realized until the solvents have entirely evaporated.

It is also possible to dispense the product as an aerosol. Suitable propellants for the composition include, for example, hydrocarbons such as n-butane or isobutane present alone or in mixtures thereof with propane; and halogenated hydrocarbons such as those sold under the trademark Freon, for example, dichlorodifluoromethane, monochlorotrifluoromethane, trichlorotrifluoroethane, dichlorotetrafluoroethane, etc.

The invention will be further illustrated by consideration of the following examples which are intended to be purely exemplary of the use of the invention.

EXAMPLE I

Methyl[2-(3-trimethoxysilylpropylamino)-ethylamino]-3-propionate (4.00 grams), and tetraethoxysilane (1.30 grams) were stirred into isopropanol (94.66 grams). Tetraisopropyl titanate (0.04 grams) was then added to the isopropanol and stirred in. The composition was packaged in a pump spray container so that the contents were closed to the atmosphere.

The formulation was sprayed onto wet hair applying approximately 0.2 cc per gram of hair, after which the hair was rolled on 5/8 inch rollers and dryed under a salon-style hair dryer for about 15 minutes. After drying, the hair was taken down from the rollers and combed into the desired style. The formulation provided a high level of set holding, even when exposed to humidities as high as 85%. The formulation formed a hard, flexible, and shiny coating on the hair, which was partially retained even after shampooing.

EXAMPLE II

| Ingredient | % by Weight |
| --- | --- |
| methyl[2-(3-trimethoxysilylpropylamino)-ethylamino]-3-propionate | 2.06 |
| Gamma-ureidopropyltriethoxysilane | 2.25 |
| Tetraethoxysilane | 1.32 |
| Tetraisopropyl titanate | 0.04 |
| Isopropanol | q.s. to 100 |

Procedure: the silanes are added to the alcohol and mixed, then the titanate is added with stirring. The solution is kept in a closed container.

EXAMPLE III

| Ingredient | % by Weight |
| --- | --- |
| N-methyl-3-aminopropyltrimethoxysilane | 4.00 |
| Tetraisopropyl titanate | 0.04 |
| Isopropanol | q.s. to 100 |

Procedure: The silane is added to the alcohol and mixed, then the titanate is added with stirring. The solution is kept in a closed container.

EXAMPLE IV

| Ingredient | % by Weight |
| --- | --- |
| Gamma-aminopropyltriethoxysilane | 3.43 |
| Tetraethoxysilane | 1.30 |
| Tetraisopropyl titanate | 0.04 |
| Isopropanol | q.s. to 100 |

Procedure: The silane is added to the alcohol and mixed, then the titanate is added with stirring. The solution is kept in a closed container.

EXAMPLE V

| Ingredient | % by Weight |
| --- | --- |
| methyl[2-(3-trimethoxysilylpropylamino)-ethylamino]-3-propionate | 3.50 |
| Tetraethoxysilane | 1.63 |
| Tetraisopropyl titanate | 0.05 |
| Stearyldimethylbenzylammonium chloride | 0.03 |
| Isopropanol | q.s. to 100 |

Procedure: the silanes are added to the alcohol and mixed, next the titanate is added with stirring. Finally, the conditioner is added with stirring. The solution is kept in a closed container.

When applied to the hair, each of the compositions of Examples II–V will result in high levels of set holding after drying, even when exposed to high humidities. The set holding will continue at a reduced level even after shampooing.

What is claimed is:

1. A method of setting hair comprising the steps of:
   (a) wetting the hair with water;
   (b) applying to the hair an effective amount of an isopropanol solution containing
      (1) from about 0.5% to about 15% by weight of at least one aminoalkylalkoxysilane having the formula $R_1NH(CH_2)_nSi(OR_2)_3$ wherein
   $R_1$ is —H, —CH$_3$, —CH$_2$NH$_2$, —(CH$_2$)$_2$NH$_2$,

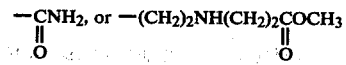

$R_2$ is methyl, ethyl, propyl, isopropyl, butyl, or isobutyl, and
   n is selected from the values 2 and 3, and
      (2) from about 0.0005% to about 1.5% by weight of a titanate ester having the formula $(R_3O)_4Ti$ wherein $R_3$ is methyl, ethyl, propyl, isopropyl, butyl, or isobutyl, and
   (c) arranging the hair in a desired configuration.

2. The method of setting hair as claimed in claim 1 in which said steps (a) and (b) are performed in reverse order.

3. A method of setting hair comprising the steps of:
   (a) wetting the hair with water;
   (b) applying to the hair an effective amount of an isopropanol solution containing
      (1) from about 0.5% to about 15% by weight of a mixture of a tetraalkoxysilane having the formula $(R_4O)_4Si$ wherein
   $R_4$ is methyl, ethyl, propyl, isopropyl, butyl, or isobutyl, and
   at least one aminoalkylalkoxysilane having the formula $R_1NH(CH_2)_nSi(OR_2)_3$ wherein
   $R_1$ is —H, —CH$_3$, —CH$_2$NH$_2$,

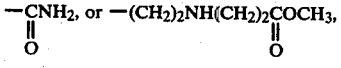

$R_2$ is methyl, ethyl, propyl, isopropyl, butyl, or isobutyl,
   n is selected from the values 2 and 3, and
      (2) from about 0.0005% to about 1.5% by weight of a titanate ester having the formula $(R_3O)_4Ti$ wherein $R_3$ is methyl, ethyl, propyl, isopropyl, butyl, or isobutyl, and (c) arranging the hair in a desired configuration.

4. The method of setting hair as claimed in claim 3 in which said steps (a) and (b) are performed in reverse order.

5. A composition for imparting set to hair comprising an isopropanol solution containing (1) from about 0.5% to about 15% by weight of at least one aminoalkylalkoxysilane having the formula $$R_1NH(CH_2)_nSi(OR_2)_3$$

wherein
$R_1$ is —H, —CH$_3$, —CH$_2$NH$_2$, —(CH$_2$)$_2$NH$_2$, $$-\underset{\underset{O}{\|}}{C}NH_2, \text{ or } -(CH_2)_2NH(CH_2)_2\underset{\underset{O}{\|}}{C}OCH_3,$$

$R_2$ is methyl, ethyl, propyl, isopropyl, butyl, or isobutyl, and
n is selected from the values 2 and 3;

(2) from about 0.0005% to about 1.5% by weight of a titanate ester having the formula $$(R_3O)_4Ti$$

wherein
$R_3$ is methyl, ethyl, propyl, isopropyl, butyl, or isobutyl,
the weight ratio of said titanate ester to said aminoalkyloxysilane being from about 1:1000 to about 1:10, and (3) a hair conditioner which is chemically inert to said aminoalkylalkoxysilane and said titanate ester.

6. The composition as claimed in claim 5 in which said hair conditioner is selected from the class consisting of quaternary ammonium compounds, pyridinium derivatives, nonreactive polysiloxanes, and paraffin oils.

7. The composition as claimed in claim 5 wherein the percent by weight of said hair conditioner is from about 0.005 to about 2.0.

8. A composition for imparting set to hair comprising an isopropanol solution containing (1) from about 0.5% to about 15% by weight of a mixture of (a) a tetraalkoxysilane having the formula $$Si(OR_4)_4$$

wherein $R_4$ is methyl, ethyl, propyl, isopropyl, butyl, or isobutyl, and (b) at least one aminoalkylalkoxysilane having the formula $$R_1NH(CH_2)_nSi(OR_2)_3$$

wherein
$R_1$ is —H, —CH$_3$, —CH$_2$NH$_2$, —(CH$_2$)$_2$NH$_2$, $$-\underset{\underset{O}{\|}}{C}NH_2, \text{ or } -(CH_2)_2NH(CH_2)_2\underset{\underset{O}{\|}}{C}OCH_3,$$

$R_2$ is methyl, ethyl, propyl, isopropyl, butyl, or isobutyl, and
n is selected from the values 2 and 3;

(2) from about 0.005% to about 1.5% by weight of a titanate ester having the formula $$(R_3O)_4Ti$$

wherein
$R_3$ is methyl, ethyl, propyl, isopropyl, butyl, or isobutyl,
the weight ratio of said titanate ester to said mixture of said tetraalkoxysilane and said aminoalkylalkoxysilane being from about 1:1000 to about 1:10, and (3) a hair conditioner which is chemically inert to said tetraalkoxysilane, said aminoalkylalkoxysilane, and said titanate ester.

9. The composition as claimed in claim 8 in which said hair conditioner is selected from the class consisting of quaternary ammonium compounds, pyridinium derivatives, nonreactive polysiloxanes, and paraffin oils.

10. The composition as claimed in claim 8 wherein the percent by weight of said hair conditioner is from about 0.005 to about 2.0.

* * * * *